United States Patent [19]
Davis et al.

[11] Patent Number: 5,489,205
[45] Date of Patent: *Feb. 6, 1996

[54] SYRINGE TIP LOCKING ASSEMBLY

[76] Inventors: Warren Davis, 942 Eldorado La., Las Vegas, Nev. 89123; David Wasserman, 2095 Mohigan Way, Las Vegas, Nev. 89109; Richard R. Matthews, 7950 Alameda St., Huntington Park, Calif. 90255

[ * ] Notice: The term of this patent shall not extend beyond the expiration date of Pat. No. 5,306,146.

[21] Appl. No.: 189,801

[22] Filed: Feb. 1, 1994

Related U.S. Application Data

[63] Continuation-in-part of Ser. No. 241,081, Sep. 6, 1988, abandoned, and a continuation-in-part of Ser. No. 351,431, May 12, 1989, Pat. No. 5,049,071, and a continuation-in-part of Ser. No. 596,987, Oct. 11, 1990, Pat. No. 5,192,206, and a continuation-in-part of Ser. No. 687,039, Apr. 16, 1991, Pat. No. 5,236,356, and a continuation-in-part of Ser. No. 4,098, Jan. 13, 1993, Pat. No. 5,342,195, and a continuation-in-part of Ser. No. 17,770, Feb. 16, 1993, Pat. No. 5,306,146.

[51] Int. Cl.[6] ................................ A61G 17/02
[52] U.S. Cl. ........................................ 433/80
[58] Field of Search .................... 433/80, 82, 88, 433/126; 604/22, 24, 283, 905, 243

[56] References Cited

U.S. PATENT DOCUMENTS

| | | | |
|---|---|---|---|
| 1,683,350 | 9/1928 | Hein | 604/243 |
| 2,828,743 | 4/1958 | Ashkenaz et al. | 604/243 |
| 4,026,025 | 5/1977 | Hunt . | |
| 4,187,848 | 2/1980 | Taylor | 604/243 |
| 4,248,589 | 2/1981 | Lewis et al. | 433/80 |
| 4,619,612 | 10/1986 | Weber et al. | 433/80 |
| 4,784,649 | 11/1988 | Imonti et al. | 604/204 |
| 4,975,054 | 12/1990 | Esrock | 433/80 |
| 4,984,984 | 1/1991 | Esrock | 433/88 |
| 5,236,356 | 8/1993 | Davis et al. | 433/80 |
| 5,306,146 | 4/1994 | Davis et al. | 433/80 |

FOREIGN PATENT DOCUMENTS

| | | |
|---|---|---|
| 1416921 | 10/1968 | Germany . |
| WO92/14434 | 9/1992 | WIPO . |
| WO92/14498 | 9/1992 | WIPO . |

OTHER PUBLICATIONS

One page ADEC brochure.

*Primary Examiner*—Cary E. O'Connor
*Attorney, Agent, or Firm*—John Edward Roethel

[57] ABSTRACT

A syringe tip is locked into a three-way dental handpiece body means of a syringe tip locking assembly that screws into a threaded receiver in the body of the handpiece. The locking assembly comprises an adaptor that has a central tapered male member that receives one end of the syringe tip, a gripping member that snaps over a raised lip on the end of the adaptor body and a locking cap that screws onto the adaptor and over the gripping member. The gripping member includes a plurality of gripping fingers that engage the syringe tip and the locking cap effects the tightening of the gripping fingers into the syringe tip. The locking assembly both applies a positive gripping action to the syringe tip and also pulls the syringe tip onto the tapered male member to securely hold the syringe tip in the adaptor during use by the dentist. The gripping member is captivated onto the raised lip of the adaptor to prevent inadvertent separation of the pieces.

9 Claims, 7 Drawing Sheets

SYRINGE TIP LOCKING ASSEMBLY

CROSS-REFERENCE TO RELATED APPLICATIONS

This application is a continuation-in-part of application Ser. No. 07/241,081, filed Sep. 6, 1988, entitled "Dental Syringe Tip and Adaptor" now abandoned; and a continuation-in-part of application Ser. No. 07/351,431, filed May 12, 1989, entitled "Dental Syringe Tip and Adaptor" now U.S. Pat. No 5,049,071; and a continuation-in-part of application Ser. No. 07/596,987, filed Oct. 11, 1990, entitled "Dental Syringe Tip and Adaptor" now U.S. Pat. No. 5,192,206; and a continuation-in-part of application Ser. No. 07/687,039, filed Apr. 16, 1991, entitled "Dental Syringe Tip and Adaptor", now U.S. Pat. No 5,236,356; and a continuation-in-part of application Ser. No. 08/004,098, filed Jan. 13, 1993, entitled "Dental Syringe Tip and Adaptor", now U.S. Pat. No. 5,342,195; and a continuation-in-part of application Ser. No. 08/017,770, filed Feb. 16, 1993, entitled "Syringe Tip Locking Assembly", now U.S. Pat. No. 5,306,146.

BACKGROUND OF THE INVENTION

This invention relates to syringe tip locking assembly for use with a syringe tip in a three-way dental handpiece assembly, and more particularly to a syringe tip locking assembly that comprises a multi-component assembly of an adaptor, a gripping member and a screw down locking cap to hold a syringe tip securely in place on a tapered male member in the adaptor when the adaptor is mounted in the handpiece of a three-way dental syringe assembly.

U.S. Pat. No. 5,049,071 (Davis et al.) discloses a disposable dental syringe tip made of plastic material. This patent also discloses various adaptors that can be used to attach the disposable syringe tip to the handpiece of a three way dental syringe assembly. The disclosure of this U.S. Pat. No. 5,049,071 is incorporated herein by this reference. Additionally, U.S. Pat. No. 5,192,206, (Davis et al.) contains additional disclosure relating to adaptors for use in three way dental syringe assemblies and the disclosure of this patent is incorporated herein by this reference.

The use of disposable plastic syringe tips has become quite widespread in light of the serious concern about the rising incidence of communicable diseases such as hepatitis and acquired immune deficiency syndrome. Dentists are taking extreme care to prevent the transmission of germs (viral or bacteria) from one patient to the next. With the conventional metal syringe tips, it was necessary to clean and sterilize the tip after each patient use. In this context, cleaning means the complete removal of all impurities and foreign matter from both the outside and the inside of the syringe tip. Cleaning must be performed first because while it is possible to clean an item without sterilizing it, it is not possible to sterilize an item without thoroughly cleaning it first. The American Dental Association states that all patient debris and bodily fluids must be removed from the instruments and surfaces before sterilization and disinfection.

The standard design of a metal syringe tip involves two metal tubes, the central metal tube completely surrounded by an outer metal tube. Fabricating a conventional metal tip results in surface defects at the junction point where the two tubes are joined together. The metal used in these tips is brass which is then chrome plated on its exterior surface. The interior brass material is extremely susceptible to corrosive deterioration. The rough interior surfaces promote the harboring of bacterial plaques and pathogens. A university study has proven that it is virtually impossible to clean the interior surfaces of a metal tip. It is axiomatic in sterilization technique, "if you can't clean it, you can't sterilize it." The processing of metal tips in the dental environment makes their current use an unacceptable answer to the problems of infection control. The disposable plastic tip is the surest way to avoid cross-contamination from patient to patient.

An analogous situation occurred with the hypodermic needle. Hypodermic needles were routinely sterilized until the early 1950's. A hepatitis epidemic, traced to contaminated hypodermic needles, advance the development of the disposable needle. Because it was impossible to preclean blood and other body fluids from the internal surface of a hypodermic needle, the need to develop a cost effective disposable needle became critical. These same concerns exist in the passageways of air/water syringe tips. Now that disposable tips are available for the air/water syringe, they will become the standard, and thus, eliminate the possibility of cross-contamination from patient to patient.

The plastic syringe tip receives air and water under pressure. It is necessary to securely hold the plastic syringe tip in the appropriate adaptor. As shown in FIG. 8 of U.S. Pat. No. 5,049,071, the end of the syringe tip is press fit over a tapered male member. Due to discrepancies and tolerances in the extrusion process, the syringe tip can partially disengage from the adaptor. This results in an inadvertent mixture of air and water when not desired.

It is an object of the present invention to provide a syringe tip locking assembly that securely holds the syringe tip in the adaptor and prevents inadvertent loosening of the syringe tip so that the air and water supply are totally separate.

It is a feature of the present invention to provide a syringe tip locking assembly that includes an adaptor, a gripping member and a locking cap. The gripping member snaps over a lip on the end of the adaptor body. The gripping member includes a plurality of gripping fingers that engage the syringe tip when the locking cap is screwed into locking position. The locking cap screws over the adaptor to effect the tightening of the gripping fingers into the syringe tip and at the same time secures and pulls the syringe tip onto the end of the tapered male member.

It is an advantage of the present invention that the plastic syringe tip will be securely held in place in the adaptor so that the air and water supply is at all times fed through the appropriate passageways in syringe tip and to inhibit the inadvertent loosening of the syringe tip from the adaptor to prevent the syringe tip from being dislodged from the handpiece.

Other objects, features and advantages will become apparent when the detailed description and drawings of the present invention are considered.

SUMMARY OF THE INVENTION

A syringe tip is locked into a three-way dental handpiece body by means of a syringe tip locking assembly that screws into a threaded receiver in the body of the handpiece. The locking assembly comprises an adaptor that has a central tapered male member that receives one end of the syringe tip, a gripping member that snaps over a lip on the end of the adaptor body and a locking cap that screws onto the adaptor and over the gripping member. The gripping member includes a plurality of gripping fingers that engage the syringe tip and an o-ring is positioned inside the gripping member. The locking cap effects the tightening of the gripping fingers and the O-ring around the syringe tip. The locking assembly both applies a positive gripping action to the syringe tip and also pulls the syringe tip onto the tapered male member to securely hold the syringe tip in the adaptor during use by the dentist. The gripping member is captivated over the end of the adaptor body to prevent inadvertent separation of the pieces.

DETAILED DESCRIPTION OF THE PREFERRED EMBODIMENTS

Figure 1:
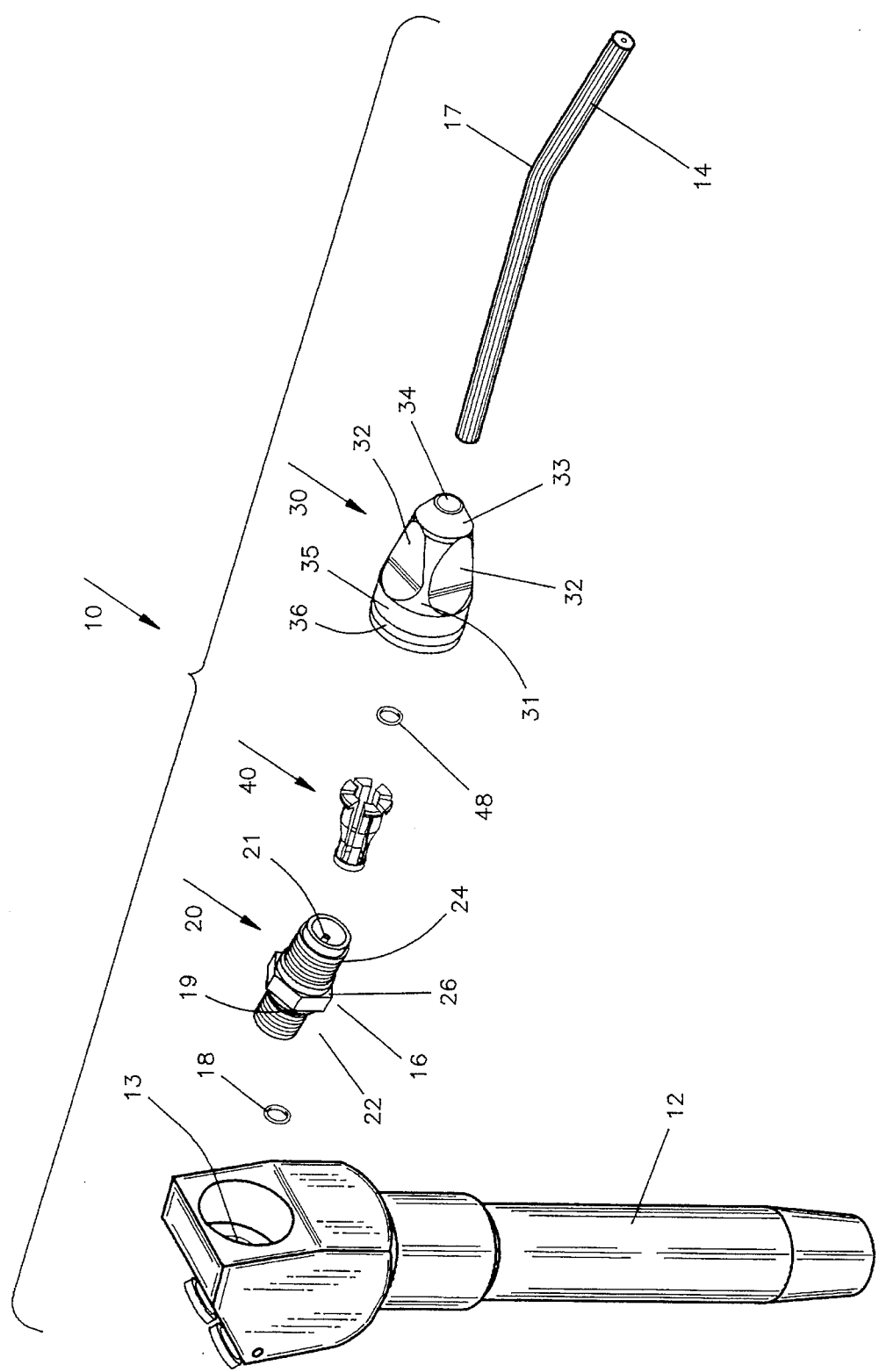
FIG. 1 shows an exploded view of a dental syringe assembly incorporating the elements of the present invention.

FIG. 1 shows at 10 the general components of a dental syringe assembly of the present invention. A handpiece body 12 has in its upper end a threaded opening 13 into which the adaptor 20 can be screwed using the first adaptor threads 22. A first O-ring 18 seals the end of the adaptor against the interior of the handpiece 12. The middle of the adaptor 20 is provided with a central hexagonal head 16 about which a wrench can be positioned to tighten the adaptor 20 into the handpiece body 12. A second O-ring 19 is provided adjacent to the first adaptor threads 22 and a third O-ring 26 is provided adjacent to the second adaptor threads 24 on the adaptor 20 to provide for an air seal.

In the preferred embodiment, the handpiece body can be a standard configuration distributed by Dental Components, Inc., 305 N. Springbrook Road, Newberry, Ore. 97132, although the adaptor 20 used in the present invention can be modified to fit any handpiece. Further details of the adaptor 20 are set out in U.S. Pat. No. 5,049,071.

The syringe tip 14 is an elongated cylindrical member preferably made of a plastic material. The syringe tip 14 is provided with a bend 17, at preferably an angle of approximately 30°, to provide easy access to any portion of the patient's mouth during use of the syringe assembly and to allow the syringe tip 14 to also function as a retractor during dental operations. The syringe tip 14 is press fit onto the tapered male member 21 of the adaptor 20. Further details of the syringe tip are set out in U.S. Pat. No. 5,049,071.

The syringe tip 14 is designed to be disposable after a single use. The tip material is fabricated in a single-step extrusion process, and is made preferably from any rigid transparent plastic. A rigid plastic is preferred to fulfill the need to use the tip for continued retraction of the cheek and tongue by the dental operator.

The adaptor 20 (shown in detail in FIGS. 3 and 4), preferably made of metal, further comprises a generally hollow body portion 25. On the interior of the hollow body 25, there is provided a baffle 23 and formed integrally with the baffle 23 is an elongated tapered male member 21. An axial opening (not shown) extends through both the baffle 23 and the tapered male member 21 to allow water from the handpiece body 12 to flow into the syringe tip 14.

Figure 2:
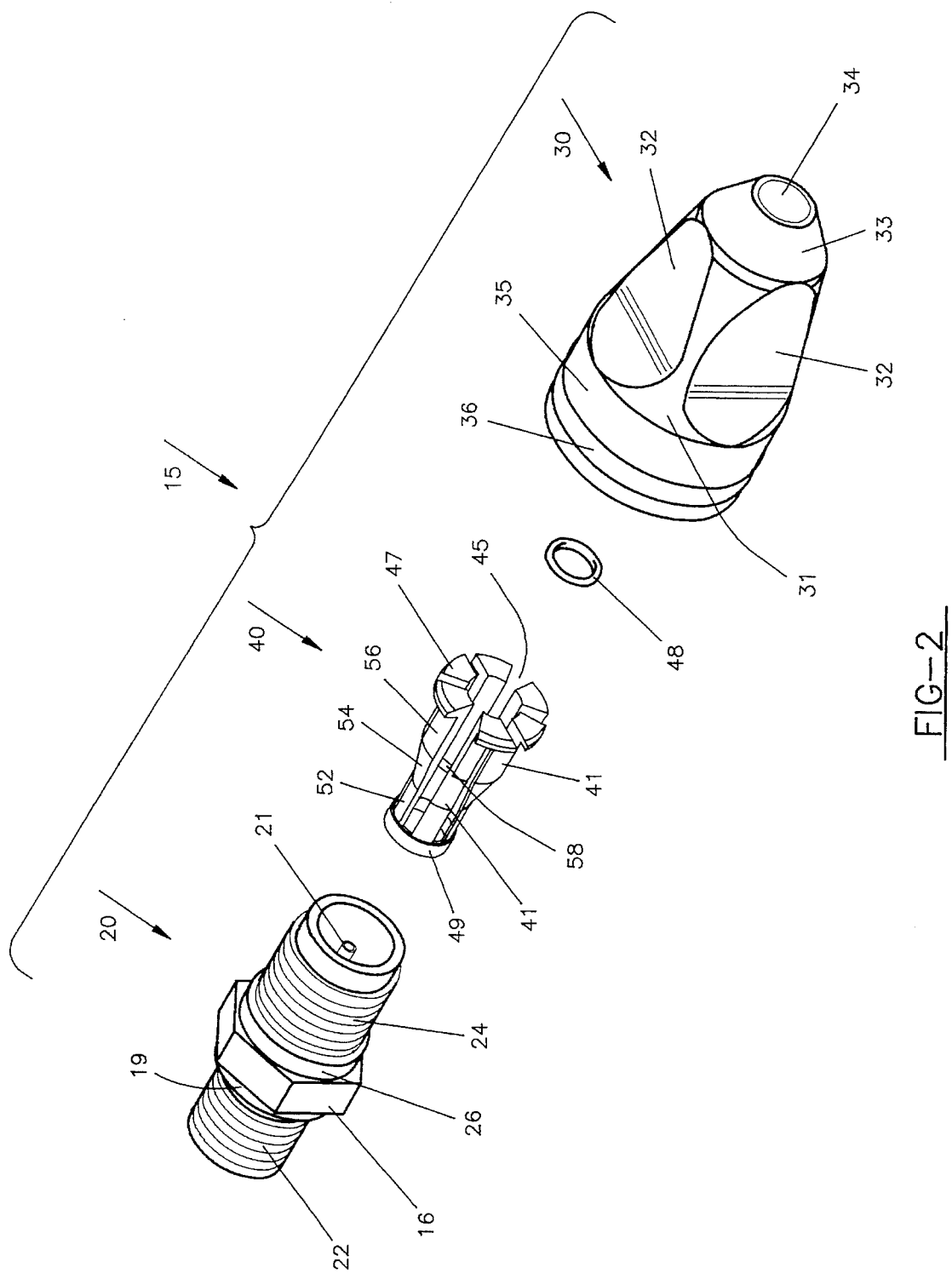
FIG. 2 shows an exploded view of an adaptor, gripping member and locking cap comprising the syringe tip locking assembly of the present invention.

FIG. 2 shows in exploded view the locking assembly 15 to securely hold the syringe tip 14 into the handpiece body 12 to prevent inadvertent loosening of the syringe tip so that the air and water supply is at all times fed through the syringe tip and to prevent the syringe tip from separating from the adaptor. The locking assembly comprises generally the adaptor 20, a gripping member 40 that fits into the interior of the adaptor 20 and over the tapered male member 21 and a locking cap 30 that screws onto the adaptor 20 and surrounds the gripping member 40.

The locking cap 30 is a generally hollow part and has a main body 31 which includes a plurality of tightening elements 32 by which the user can easily grip and turn the locking cap 30 to screw the locking cap 30 onto the adaptor 20. As shown the tightening elements 32 can be beveled sections, although any other conventional tightening elements can be used such as serrated or roughened areas on the main body 31. One end of the locking cap 30 has a narrow cone-shaped end 33 with an aperture 34 to receive one end of the syringe tip 14. The other end of the locking cap 30 has a wide end 35 that includes a channel 36 to receive a fourth O-ring 37. The fourth O-ring 37 provides a seal against air leaking from the assembly as well as a dirt barrier to prevent contaminants entering the interior of the assembly.

Figure 3:
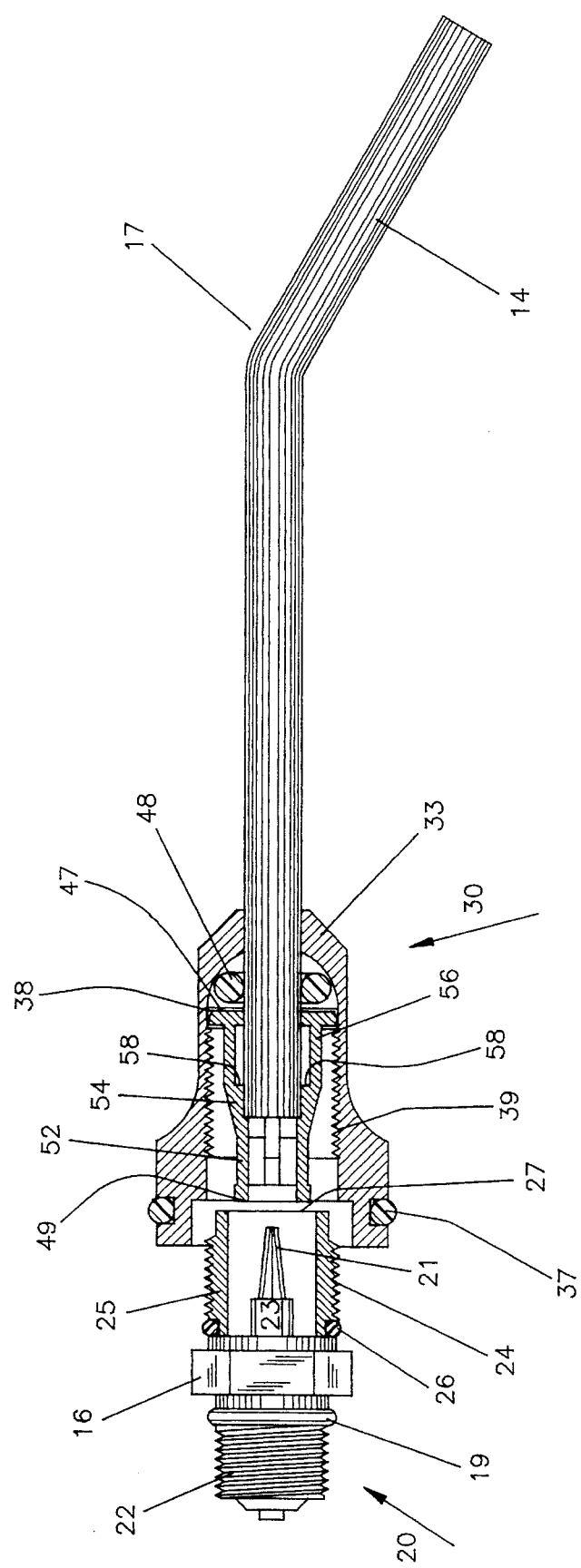
FIG. 3 shows a cross-sectional view of the syringe tip locking assembly of the present invention with a syringe tip mounted therein in an unlocked position.
Figure 4:
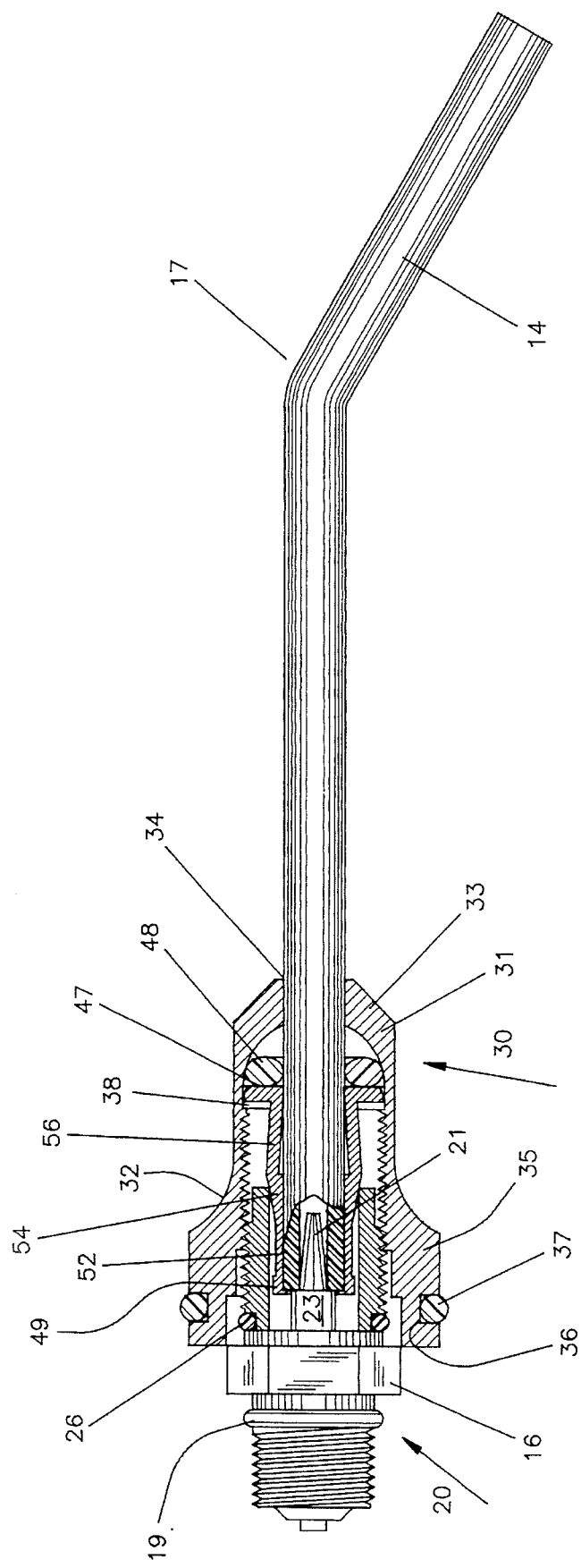
FIG. 4 shows a cross-sectional view of the syringe tip locking assembly of the present invention with the syringe tip mounted therein in the locked position.

As shown in detail in FIGS. 3 and 4, the interior of the locking cap 30 has a threaded section 39 which is sized to interfit with the second adaptor threads 24 on the adaptor 20. Toward the narrow end 33 of the locking cap 30 and adjacent the threaded section 39 there is provided an internal bore 38 into which is mounted the end flange 47 of the gripping member 40. Also on the interior of the locking cap 30 adjacent the internal bore 38 is a rounded cavity that receives the fifth O-ring 48.

Shown in detail in FIG. 2, the gripping member 40 is a generally hollow body and includes a plurality of fingers 41 separated by longitudinal slots 45. Each finger 41 has three sections—a smaller straight section 52, a central tapered section 54 and a larger straight section 56. The ends of the smaller straight section 52 join at the end connector 49. The ends of the larger straight section 56 each have an outwardly turned end flange 47 that fit into the internal bore 38 on the interior of the locking cap 30. This configuration loosely holds and captivates the gripping member 40 in the internal bore 38 of the locking cap 30 so that these two pieces do not become separated during use by the dentist.

On the interior of each of the fingers 41, there is provided gripping flange 58. When the gripping member 40 is compressed around the syringe tip 14, the gripping flange 58 will dig into the plastic material of the syringe tip 14 and assist in the gripping of the syringe tip 14 by the gripping member 40.

FIG. 3 shows the locking assembly of the present invention in its unlocked position. The dentist takes a new syringe tip 14 and slides it into the aperture 34 of the locking cap 30 and down into the interior of the locking cap 30 until the end of the syringe tip 14 abuts against the smaller straight section 52 of the gripping member 40. The dentist then grips the locking cap 30 and screws it onto the second adaptor threads 24 of the adaptor 20.

As shown in FIG. 4, as the locking cap 30 moves along the second adaptor threads 24, each of the fingers 41 compress around the end of the syringe tip 14. The end 27 of the hollow body 25 of the adaptor 20 slides along the exterior of the central tapered section 54 of each finger 41 and forces the finger 41 to collapse toward the syringe tip 14. The longitudinal slots 45 provide the room for the fingers 41 to collapse toward the syringe tip 14. The gripping flanges 58 dig into the plastic surface of the syringe tip 14.

The continued threading of the locking cap 30 onto the second adaptor threads 24 also pulls the end of the syringe tip onto the tapered male member 21. The combination of the gripping of the syringe tip 14 by the fingers 41 and the pulling of the syringe tip 14 onto the tapered male member provides a most secure and quite tight fitting of the syringe tip 14 into the adaptor 20. This tight fitting inhibits any movement or loosening of the syringe tip 14 from the adaptor 20 during the injection of air and water from the handpiece body 12 during use by the dentist.

The movement of the locking cap 30 onto the second threads 24 also causes the end flanges 47 on the gripping member 40 to press against the fifth O-ring 48. This movement compresses the fifth O-ring 48 around the syringe tip 14 as shown in FIG. 4 and also assist in securely holding the syringe tip 14 on the tapered male member 21 of the adaptor 20.

The replacement of the used syringe tip 14 with a new one is quite simple. The dentist merely loosens the locking cap 30 from the adaptor 20 by unscrewing the locking cap 30. This releases the pressure of the fingers 41 around the syringe tip 14 and allows the syringe tip 14 to disconnect from the tapered male member 21. The used syringe tip 14 is removed from the locking cap 30 and replaced with a new syringe tip 14 for the next patient.

Figure 5:
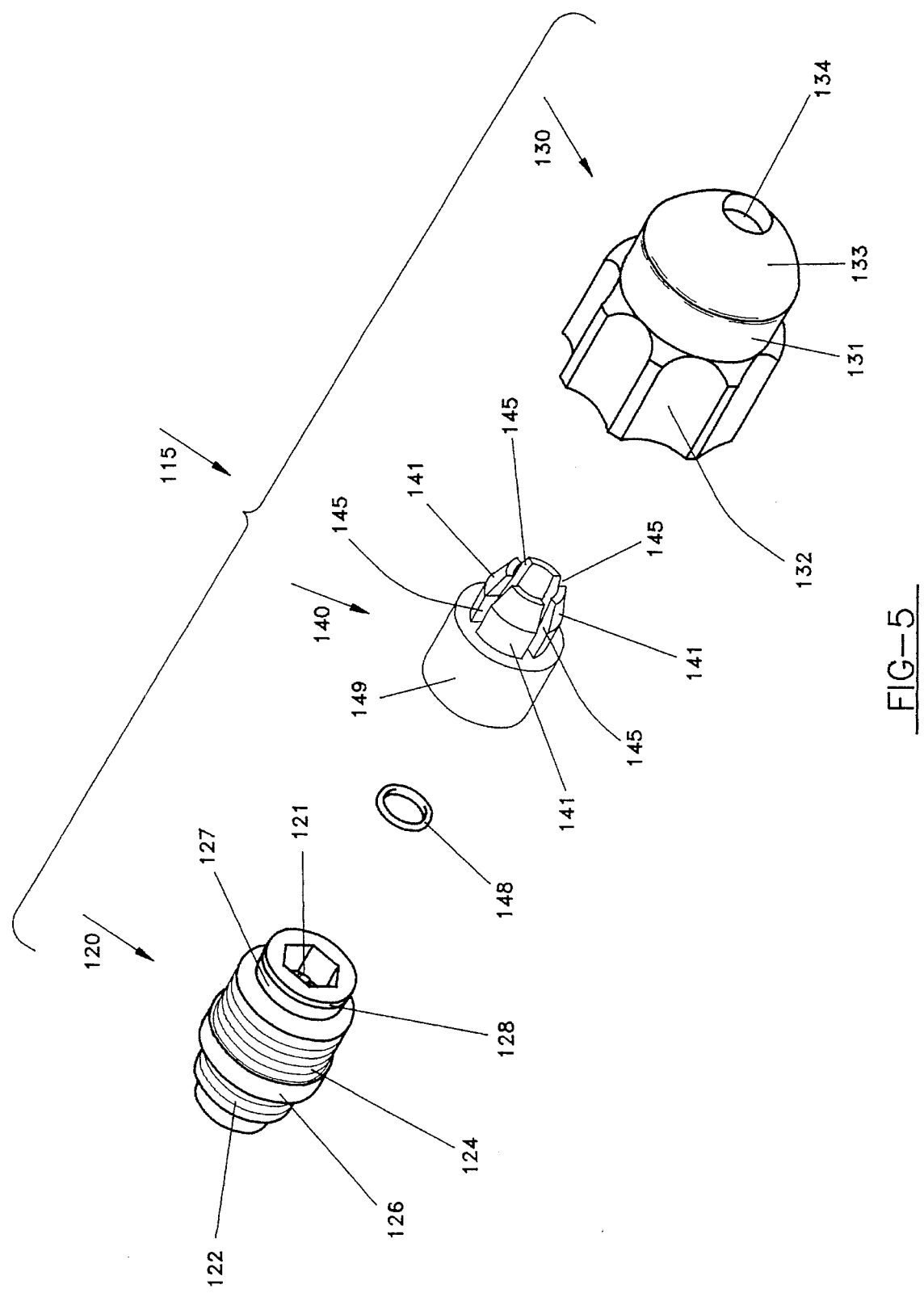
FIG. 5 shows an exploded view of an alternative adaptor, alternative gripping member and alternative locking cap comprising the alternative syringe tip locking assembly of the present invention.

FIG. 5 shows in exploded view another embodiment of a locking assembly 115 to securely hold the syringe tip into the handpiece body to prevent inadvertent loosening of the syringe tip so that the air and water supply is at all times fed through the syringe tip and to prevent the syringe tip from separating from the adaptor. The locking assembly 115 comprises generally the adaptor 120, a gripping member 140 that fits over the exterior end of the adaptor 120 and a locking cap 130 that screws onto the adaptor 120 and surrounds the gripping member 140.

The adaptor 120 (shown in FIGS. 5 and 6) comprises a generally hollow body portion 125 and on the interior of the hollow body 125, there is provided a baffle 123 and formed integrally with the baffle 123 is an elongated tapered male member 121. An axial opening (not shown) extends through both the baffle 123 and the tapered male member 121 to allow water from the handpiece body 112 to flow into the syringe tip. The adaptor 120 is screwed into the handpiece body (not shown) using the first adaptor threads 122. A first O-ring (not shown) seals the end of the adaptor against the interior of the handpiece 12. A second O-ring (Not shown) is provided adjacent to the first adaptor threads 122 and a third O-ring 126 is provided adjacent to the second adaptor threads 124 on the adaptor 120 to provide for an air seal. Further details of the adaptor are shown in U.S. Pat. No. 5,049,071 (Davis et al.), which is incorporated herein by reference.

A raised lip 128 extends around the entire circumference of the exterior of the open end 127 of the adaptor 120 located adjacent the second adaptor threads 124. This raised lip 128 cooperates with a similar lip on the gripping member 140 as will be explained to hold the gripping member 140 on the adaptor 120 when in use.

The locking cap 130 is a generally hollow part and has a main body 131 which includes a plurality of flutes or tightening elements 132 by which the user can easily grip and turn the locking cap 130 to screw the locking cap 130 onto the adaptor 120. As shown in FIG. 5, in this preferred embodiment eight equally spaced flutes 132 are disposed around the circumference of the locking cap, although any number of flutes 132 may be use as well as other conventional tightening elements such as serrated or roughened areas on the main body 131. One end of the locking cap 130 has a narrow rounded conical-shaped end 133 with an aperture 134 to receive one end of the syringe tip 114.

Figure 6:
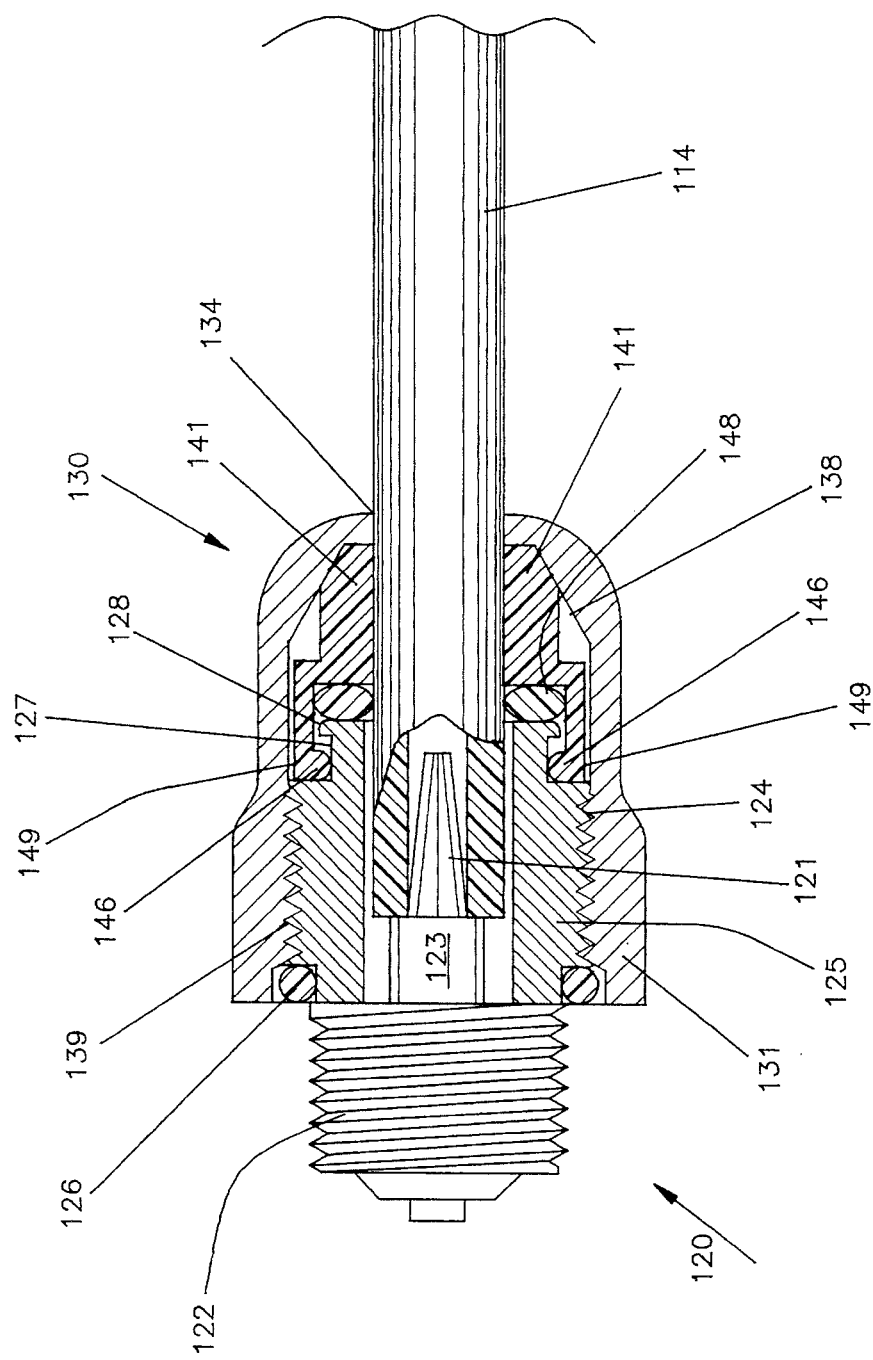
FIG. 6 shows a cross-sectional view of the alternative syringe tip locking assembly shown in FIG. 5 with the syringe tip mounted therein in the locked position.
Figure 7:
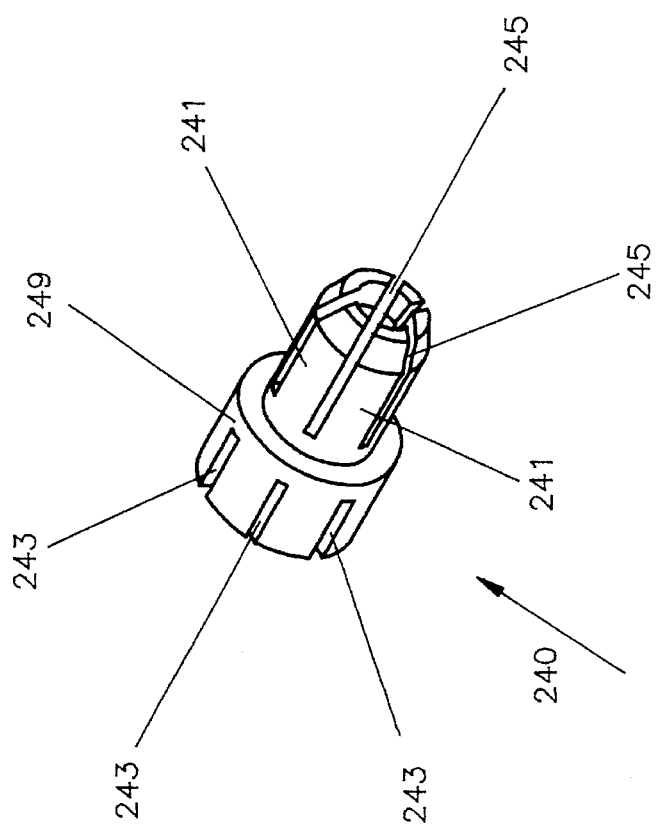
FIG. 7 shows an isometric view of another alternative gripping member used in the present invention.

As shown in detail in FIG. 6, the interior of the locking cap 130 has a tapered internal bore 138 that interacts with the gripping member 140 and a threaded section 139 which is sized to interfit with the second adaptor threads 124 on the adaptor 120.

Shown in detail in FIGS. 5 and 6, the gripping member 140 is a generally hollow body and includes a plurality of fingers 141 separated by longitudinal slots 145. One end of each of the fingers 141 is attached to the base 149. On the interior of the base 149 of the gripping member 140, there is provided a lip 146 that extends around the entire interior circumference of the gripping member 140. The fourth O-ring 148 is positioned on the interior of the hollow body inside the fingers 141.

In this preferred embodiment of the invention, the gripping member 140 is made of a material having the ability to slightly flex under force, but still return to its original shape when the force is removed, such as a plastic like polysulfone, nylon or Delrin or a metal like spring steel. This capability of the material allows the base 149 of the gripping member 140 to be pushed over the lip 128 of the adaptor. The circumferential lip 146 on the interior of the gripping member 140 will slide past the raised lip 128 on the exterior of the end 127 of the adaptor 120 as shown in FIG. 6. This configuration loosely holds and captivates the gripping member 140 around the end 127 of the adaptor 120 so that these two pieces do not become separated during use by the dentist.

The ends of the fingers 141 fit up inside the locking cap 130 when the locking cap is screwed onto the adaptor 120. As shown in FIG. 6, as the locking cap 130 is screwed onto the second adaptor threads 124, each of the fingers 141 compress around the end of the syringe tip 114. The longitudinal slots 145 provide the room for the fingers 141 to collapse toward the syringe tip 114. The fourth seal 148 compresses and, along with the effect of the fingers 141 also being compressed, the syringe tip 114 is tightly held and pulled onto the tapered male member 123.

FIG. 8 shows another alternative embodiment of the present invention. This embodiment provides for an alternative gripping member 240 that can also be snapped over the raised lip 128 on the open end 127 of the adaptor 120 shown in FIGS. 5 and 6. This alternative gripping member 240 is a generally hollow body and includes a plurality of fingers 241 separated by first longitudinal slots 245. One end of each of the fingers 241 is attached to the base 249. On the interior of the end connector 249 of the gripping member 240, there is provided a lip (not shown, but like the lip 146 shown in FIG. 6) that extends around the entire interior circumference of the gripping member 240. A fourth O-ring (not shown) is positioned on the interior of the hollow body inside the fingers 241.

If the gripping member 240 is made out of a material (such as brass) that does not have sufficient flexibility, then the base 249 of the gripping member 240 is provided with a plurality of second longitudinal slots 243 which will allow the base 249 to expand enough to allow the gripping member to simply snap over the raised lip 128 on the open end 127 of the adaptor 120.

While the invention has been illustrated with respect to several specific embodiments thereof, these embodiments should be considered as illustrative rather than limiting. Various modifications and additions may be made and will be apparent to those skilled in the art. Accordingly, the invention should not be limited by the foregoing description, but rather should be defined only by the following claims.

We claim:

1. A locking assembly for locking a syringe tip in a dental handpiece body comprising:
    a) an adaptor mounted in the handpiece body, the adaptor including a hollow body portion having external threads and a tapered male member mounted on the interior of the hollow body portion;
    b) a raised lip extending circumferentially and exteriorly around an open end of the hollow body;
    c) a gripping member comprising a generally hollow tubular body separated into a plurality of fingers, each finger separated from an adjacent finger by a longitudinal slot;
    d) a raised lip extending circumferentially and interiorly around an open end of the gripping member;
    e) the open end of the gripping member being mounted onto the open end of the hollow body of the adaptor; and
    f) a locking cap comprising a generally hollow body having internal threads;
    whereby when the locking cap is screwed onto the adaptor, the gripping member compresses around a syringe tip to securely hold the syringe tip inside the adaptor.

2. The locking assembly of claim 1 in which an O-ring is mounted in an interior of the hollow body of the gripping member whereby each finger compresses the O-ring around the syringe tip when the locking cap is screwed onto the adaptor.

3. The locking assembly of claim 1 in which an O-ring is mounted in an interior of the hollow body of the gripping member whereby each finger compresses the O-ring around the syringe tip when the locking cap is screwed onto the adaptor.

4. dental syringe assembly comprising:
    a) a dental handpiece body, and
    b) a locking assembly for locking a syringe tip in a dental handpiece body comprising
        1) an adaptor mounted in the handpiece body, the adaptor including a hollow body portion having external threads and a tapered male member mounted on the interior of the hollow body portion;
        2) a raised lip extending circumferentially and exteriorly around an open end of the hollow body;
        3) a gripping member comprising a generally hollow tubular body separated into a plurality of fingers, each finger separated from an adjacent finger by a longitudinal slot;
        4) a raised lip extending circumferentially and interiorly around an open end of the gripping member;
        5) the open end of the gripping member being mounted onto the open end of the hollow body of the adaptor; and
        6) a locking cap comprising a generally hollow body having internal threads;
    whereby when the locking cap is screwed onto the adaptor, the gripping member compresses around a syringe tip to securely hold the syringe tip inside the adaptor.

5. The dental syringe assembly of claim 3 further including a syringe tip mounted in the adaptor and locked therein by the locking assembly.

6. A syringe tip adaptor for connecting a syringe tip to a handpiece body comprising;
    a) a generally cylindrical body having a hollow interior;
    b) means for connecting the cylindrical body to the handpiece body;
    c) a baffle mounted within the hollow interior of the cylindrical body;
    d) a tapered male connector formed integrally with the baffle and having an axial opening therethrough adapted to cooperate with a central passageway in a syringe tip to provide a water passageway from the handpiece through the adaptor and into the syringe tip whereby when a syringe tip is mounted on the tapered male connector, the syringe tip will be tightly held on the tapered male connector to prevent axial rotation of the syringe tip and to ensure that the air and water passageways do not leak into each other; and
    e) a raised lip extending circumferentially and exteriorly around an open end of the hollow body and adapted to cooperate with a syringe tip locking assembly to securely hold a syringe tip onto the tapered male connector.

7. The adaptor of claim 6 further comprising screw threads on the exterior surface of the cylindrical body for connecting the cylindrical body to a syringe tip locking assembly.

8. A dental syringe assembly comprising a handpiece body including means for mounting a syringe tip assembly to the handpiece body, said syringe tip assembly comprising
    a) a syringe tip adaptor for connecting a syringe tip to a handpiece body comprising
        1) a generally cylindrical body having a hollow interior;
        2) means for connecting the cylindrical body to the handpiece body;
        3) a baffle mounted within the hollow interior of the cylindrical body;
        4) a tapered male connector formed integrally with the baffle and having an axial opening therethrough adapted to cooperate with a central passageway in a syringe tip to provide a water passageway from the handpiece through the adaptor and into the syringe tip whereby when a syringe tip is mounted on the tapered male connector, the syringe tip will be tightly held on the tapered male connector to prevent axial rotation of the syringe tip and to ensue that the air and water passageways do not leak into each other; and
        5) a raised lip extending circumferentially and exteriorly around an open end of the hollow body and adapted to cooperate with a syringe tip locking assembly to securely hold a syringe tip onto the tapered male connector; and
    b) a syringe tip mounted on the syringe tip adaptor.

9. The adaptor of claim 8 further comprising screw threads on the exterior surface of the cylindrical body for connecting the cylindrical body to a syringe tip locking assembly.

* * * * *